United States Patent
Flagan et al.

(10) Patent No.: US 9,138,663 B2
(45) Date of Patent: Sep. 22, 2015

(54) OPPOSED MIGRATION AEROSOL CLASSIFIER GAS AND HEAT EXCHANGER

(71) Applicant: California Institute of Technology, Pasadena, CA (US)

(72) Inventors: Richard C. Flagan, Pasadena, CA (US); Wilton Mui, Pasadena, CA (US); Andrew J. Downard, Los Angeles, CA (US)

(73) Assignee: California Institute of Technology, Pasadena, CA (US)

( * ) Notice: Subject to any disclaimer, the term of this patent is extended or adjusted under 35 U.S.C. 154(b) by 283 days.

(21) Appl. No.: 13/768,817

(22) Filed: Feb. 15, 2013

(65) Prior Publication Data
US 2013/0213860 A1 Aug. 22, 2013

Related U.S. Application Data

(60) Provisional application No. 61/600,434, filed on Feb. 17, 2012.

(51) Int. Cl.
| | |
|---|---|
| *G01N 15/00* | (2006.01) |
| *G01N 1/40* | (2006.01) |
| *B01D 21/00* | (2006.01) |
| *G01N 15/02* | (2006.01) |

(52) U.S. Cl.
CPC ............ *B01D 21/00* (2013.01); *G01N 15/0266* (2013.01); *G01N 2015/0046* (2013.01)

(58) Field of Classification Search
USPC ............ 95/57–81; 96/3, 52, 64; 209/132–734
See application file for complete search history.

(56) References Cited

U.S. PATENT DOCUMENTS

| | | | | |
|---|---|---|---|---|
| 4,147,621 A | * | 4/1979 | Giddings | 210/637 |
| 4,214,981 A | * | 7/1980 | Giddings | 209/155 |
| 4,737,268 A | * | 4/1988 | Giddings | 209/12.2 |
| 4,830,756 A | * | 5/1989 | Giddings | 210/239 |

(Continued)

FOREIGN PATENT DOCUMENTS

EP 2352008 8/2011

OTHER PUBLICATIONS

PCT International Search Report and Written Opinion dated May 27, 2013 for PCT Application No. PCT/US2013/026499.

(Continued)

*Primary Examiner* — Duane Smith
*Assistant Examiner* — Sonji Turner
(74) *Attorney, Agent, or Firm* — Gates & Cooper LLP

(57) ABSTRACT

A method is provided for changing a property of a sample. A sample, comprising particles suspended within a sample fluid, is introduced into a channel which comprises two walls that are permeable to a flow of fluid. A cross-flow is introduced at a predetermined temperature and of a predetermined chemical composition into the channel through a wall. This cross-flow flows at a first velocity and exits in a first direction through the other wall. An imposed field is applied on the particles in a second direction counter to the first direction of the cross-flow. The imposed field causes the particles to migrate at a second velocity opposite and/or equal to the first velocity of the cross-flow. Particles that are approximately balanced by the first and second velocities travel through the channel and are discharged in a fluid of predetermined chemical composition and at the predetermined temperature of the cross-flow.

20 Claims, 12 Drawing Sheets

(56) References Cited

U.S. PATENT DOCUMENTS

| | | | |
|---|---|---|---|
| 4,894,146 A * | 1/1990 | Giddings | 209/12.2 |
| 4,894,172 A * | 1/1990 | Williams | 210/748.01 |
| 5,133,844 A * | 7/1992 | Stevens | 204/549 |
| 6,365,050 B1 * | 4/2002 | Cauchon | 210/635 |
| 6,905,029 B2 * | 6/2005 | Flagan | 209/210 |
| 7,141,152 B2 * | 11/2006 | Le Febre | 204/450 |
| 7,199,362 B2 * | 4/2007 | Rockwood et al. | 250/286 |
| 8,360,244 B2 * | 1/2013 | Wyatt et al. | 209/156 |
| 8,384,897 B2 * | 2/2013 | Mizukami et al. | 356/335 |
| 2003/0226754 A1 * | 12/2003 | Le Febre | 204/451 |
| 2004/0050756 A1 * | 3/2004 | Flagan | 209/156 |
| 2005/0006578 A1 * | 1/2005 | Rockwood et al. | 250/289 |
| 2006/0266132 A1 | 11/2006 | Cheng et al. | |
| 2008/0060457 A1 * | 3/2008 | Liu et al. | 73/863.31 |
| 2009/0173670 A1 | 7/2009 | Okuda et al. | |
| 2011/0019187 A1 * | 1/2011 | Mizukami et al. | 356/335 |
| 2011/0155650 A1 * | 6/2011 | McNeil-Watson | 209/155 |

OTHER PUBLICATIONS

Liu, B., et al., Aerosol Mobility Chromatograph—New Detector for Sulfuric-Acid Aerosols. Atmos Environ, 1978, 12 (1-3): p. 99-104.

Rader, D. et al., Application of the Tandem Differential Mobility Analyzer to Studies of Droplet Growth or Evaporation. J Aerosol Sci, 1986, 17(5): p. 771-787.

Flagan, R., Opposed migration aerosol classifier (OMAC), Aerosol Science and Technology, 2004, 38(9): p. 890.

Downard, A. et al., An Asymptotic Analysis of Differential Electrical Mobility Classifiers, Aerosol Science and Technology, 2011, p. 717-729.

Knutson, E. et al., Aerosol classification by electric mobility: apparatus, theory, and applications, J Aerosol Sci, 1975, p. 443-451.

Tammet, H., Symmetric Inclined Grid Mobility Analyzer for the Measurement of Charged Clusters and Fine Nanoparticles in Atmospheric Air, Aerosol Science and Technology, 2011, p. 468-479.

* cited by examiner

OPPOSED MIGRATION AEROSOL CLASSIFIER GAS AND HEAT EXCHANGER

CROSS-REFERENCE TO RELATED APPLICATIONS

This application claims the benefit under 35 U.S.C. Section 119(e) of the following commonly-assigned U.S. provisional patent application, which is incorporated by reference herein:

Provisional Application Ser. No. 61/600,434, filed on Feb. 17, 2012, by Richard C. Flagan et al., entitled "OPPOSED MIGRATION AEROSOL CLASSIFER GAS AND HEAT EXCHANGER,".

This application is also related to the following commonly-assigned patent and patent applications, which are incorporated by reference herein:

U.S. Pat. No. 6,905,029, issued on Jun. 14, 2005, by Richard C. Flagan, entitled "CROSS-FLOW DIFFERENTIAL MIGRATION CLASSIFIER,"; and U.S. patent application Ser. No. 13/769,122, filed on Feb. 15, 2013, by Richard C. Flagan et al., entitled "RADIAL OPPOSED MIGRATION AEROSOL CLASSIFIER WITH GROUNDED AEROSOL ENTRANCE AND EXIT,", which claims priority to Provisional Application Ser. No. 61/600,409, filed on Feb. 17, 2012, by Richard C. Flagan et al., entitled "RADIAL OPPOSED MIGRATION AEROSOL CLASSIFIER WITH GROUNDED AEROSOL ENTRANCE AND EXIT,".

BACKGROUND OF THE INVENTION

1. Field of the Invention

The present invention relates generally to methods, apparatuses, and articles of manufacture for changing a property of a sample, and in particular, for changing a temperature, particle size, and/or chemical composition of a fluidic sample with an opposed migration aerosol classifier (OMAC).

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is incorporated by reference herein.)

A number of different systems and techniques have been developed for separating and measuring particles contained in fluids such as gases (e.g. aerosols or atmospheric ultrafine particles) and liquids (e.g. colloids or suspensions). Common systems and techniques in the art include the usage of condensation particle counters (CPC) and differential electrical mobility classifiers (DEMC) such as differential mobility analyzers (DMA) and inclined grid mobility analyzers (IGMA). Such systems separate and measure particles according to specific particle properties/characteristics, for example a size, mass or charge of the particle. The systems may also separate and measure particles based on a change in a specific property/characteristic of the particles (e.g. size, mass, charge) when the particles are subjected to certain conditions and environments.

One exemplary application for DMAs in tandem measurements (i.e. tandem differential mobility analysis) is to probe for particle properties such as hygroscopicity and volatility [1, 2]. A typical tandem DMA setup comprises a fixed-voltage DMA that supplies a substantially monodisperse aerosol sample. The temperature and/or vapor composition is then changed, typically by flowing the sample through a denuder or a heated tube. The particles respond to this changed environment, and the extent to which they grow or shrink is determined by using a second DMA operating in scanning mode.

Independent of the system used, oftentimes the greatest difficulty in separating and measuring particles with changing environments is the different time histories of the particles as they traverse the intermediate step where a sample property, such as the temperature or composition, is changed. For example, temperature and vapor changes respectively rely on diffusion from and to the walls of the system, which is often a comparatively slow process relative to the sample flow through the system. Furthermore, particles that are near the walls may experience a substantially different environment as compared to those further away from the walls of the system. Thus, a final measured signal is often an amalgamation of particles subject to inconsistent conditions and environments under a wide range of time histories. Therefore, the effect of changing a property of a sample is difficult to measure and quantify with great certainty and the separation or measurement of specific particles is equally frustrated.

In view of the above, there is a need for a method, apparatus, and article of manufacture for rapidly changing sample properties, such as the fluid temperature, particle size, and/or fluid chemical composition. Furthermore, there is a need for a method, apparatus, and article of manufacture for performing tandem mobility analysis that subjects particles in a sample to uniform conditions and environments under more consistent time histories, which will allow for more easily quantifiable separations and measurements.

SUMMARY OF THE INVENTION

The invention provided herein has a number of embodiments useful, for example, in changing a property of a sample. According to one or more embodiments of the present invention, a method, apparatus, and article of manufacture are provided for rapidly changing a sample property, such as the fluid temperature, particle size, and/or fluid chemical composition, using an opposed migration aerosol classifier (OMAC).

In one aspect of the present invention, a method for changing a property of a sample is provided. The method comprises introducing a sample, comprising one or more particles suspended within a sample fluid, through a channel. The channel comprises two walls that are permeable to a flow of fluid. A fluid cross-flow of predetermined chemical composition is introduced at a predetermined temperature to the channel through one of the permeable walls. This cross-flow flows at a first velocity and exits in a first direction through the other permeable wall. An imposed field (where the field can be an electric, magnetic, thermal, gravitational field, amongst others) is applied on the one or more particles in the sample in a second direction counter to the first direction of the cross-flow. The imposed field causes the one or more of the particles of desired size and/or charge to migrate at a second velocity opposite and/or equal to a first velocity of the cross-flow. The particles that travel through the channel are discharged. Furthermore, the particles that travel through the channel are discharged at the predetermined temperature of the cross-flow fluid. In one or more embodiments, the sample fluid is substantially replaced by the cross-flow fluid as the sample flows through the channel. Therefore, the discharged particles that travel through the channel are no longer suspended within the sample fluid but are rather suspended within the cross-flow fluid.

In certain embodiments of the invention, the cross-flow fluid, which may contain one or more trace vapors, replaces a trace vapor in the sample fluid. In further embodiments of the invention, a size of the one or more particles of the sample is changed while the one or more particles travel through the channel due to a difference in the sample fluid and cross-flow fluid temperatures and/or a difference in the concentration of one or more vapors in the sample fluid and the cross-flow fluid. In still other embodiments, the chemical composition of the sample fluid is changed while the one or more particles of the sample travel through the channel.

BRIEF DESCRIPTION OF THE DRAWINGS

Referring now to the drawings in which like reference numbers represent corresponding parts throughout.

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

An opposed migration aerosol classifier (OMAC) is an excellent option for nanoparticle classification in the gas phase [3]. Its performance is favorable relative to other alternatives in that it is well suited for classifying sub-10 nm aerosol and gas ions. Additionally, OMAC instruments may be made with a more compact footprint than the commonly used alternative of differential mobility analyzers (DMA) [4-6]. Thus, in one exemplary implementation, an OMAC may be used in tandem mobility analysis as a replacement to a first stage DMA. An OMAC may also be used as a replacement to a second stage DMA, though the design of a scanning OMAC is more complex.

In one aspect of the present invention, methods and systems are provided using an OMAC for replacing the diffusion-based methods currently used for changing fluid sample properties. These methods and systems that are related to the OMAC rely on the advection of a fluid sample through cross-flows and imposed fields, which are both considerably faster than diffusion, to change various properties of the sample and the particles within the sample. Thus, for example, OMACs are excellent for rapid gas exchange when compared to other mobility analyzers. For an aerosol sample, the aerosol inlet gas is rejected from the system almost immediately and replaced by a desired cross-flow gas, thereby rapidly changing the properties of the sample.

Though the usage of an OMAC is described in various embodiments of the invention as follows, other differential electrical mobility classifiers (DEMC) may also be used for changing the properties of a sample, such as rapidly changing the gas temperature and/or composition in which a charged aerosol is suspended. Suitable DEMCs include, but are not limited to, OMACs, DMAs, and IGMAs of planar, radial, coaxial cylindrical, conical, and other geometries. For example, an inclined grid mobility analysis (IGMA) may be used since, similar to an OMAC, it also shares favorable up-scaling in performance metrics when compared to DMAs [7].

Logical Flow

Figure 1:
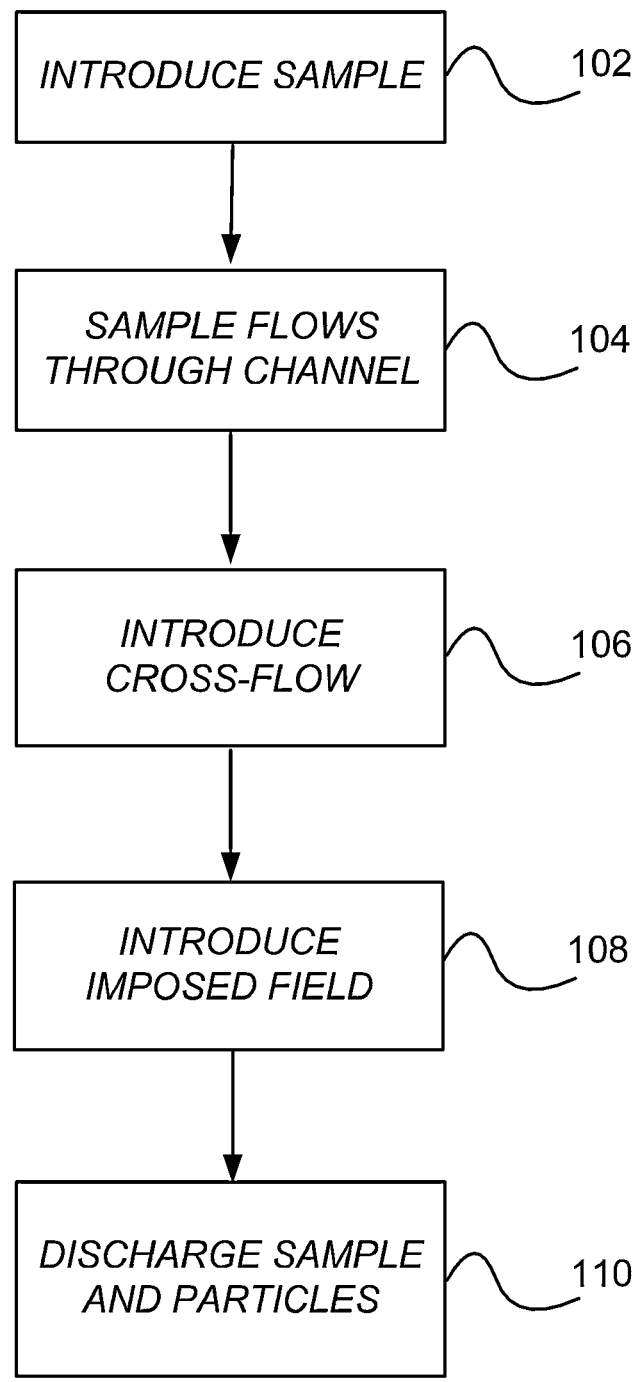
FIG. 1 is a flow chart illustrating a logical flow for changing a property of a sample in accordance with one or more embodiments of the invention.

FIG. 1 is a flow chart illustrating a logical flow 100 for changing a property of a sample in accordance with one or more embodiments of the invention. At block 102, a sample, comprising one or more particles suspended within a sample fluid, is introduced into a channel. The sample may be a variety of substances in a variety of forms. For example, the sample may take the form of an aerosol, gas mixture, colloid, suspension of particles in a fluid, or liquid solution. Furthermore, the sample may be a polydisperse sample (i.e. comprising particles of various size, shape, and/or mass) or may be a monodisperse sample (i.e. comprising particles of uniform size, shape, and/or mass). The sample may also include trace vapors that are also introduced when the sample is injected or pumped into the channel. The channel has two or more walls that are permeable to the flow of fluid (liquid or gas). In one or more embodiments, the channel is part of a classification region of an opposed migration aerosol classifier (OMAC) or radial opposed migration aerosol classifier (ROMAC).

At block 104, the sample flows through the channel between the two or more permeable walls. A pressure difference between the inlet/entrance region (i.e. where the sample is introduced) and outlet/exit region (i.e. where the sample is discharged) of the channel causes the sample to flow in one general direction through the channel. In one or more embodiments the sample flow is laminar.

At block 106, a cross-flow at a predetermined temperature is introduced to the channel through one of the permeable walls. The cross-flow may also be a variety of substances in a variety of forms. For example, the cross-flow may be a liquid, gas, or comprise solids suspended in a fluid, etc. The cross-flow flows at a first velocity and exits in a first direction through the other permeable wall. In one or more embodiments, the cross-flow exits the channel through a wall directly opposite the wall it is introduced through. As the cross-flow exits the channel, the cross-flow forces the initial sample fluid to exit along with it through the permeable wall. Therefore, the sample fluid of the sample is replaced by the cross-flow as the sample flows through the channel. By replacing the sample fluid with the cross-flow, any trace vapors that were introduced along with the sample will also be forced out through the permeable wall. Moreover, the predetermined temperature of the cross-flow replaces and changes the temperature of the sample and its particles.

At block 108, an imposed field is applied in a second direction that is counter to the first direction of the cross-flow. In one or more embodiments, the direction of the imposed field is orthogonal to the direction of the flow of the cross-flow. The imposed field causes the targeted particles in the sample to migrate at a velocity that is opposite and/or equal in magnitude to the velocity of the cross-flow. Therefore, as the cross-flow forces the sample fluid to exit along with it through the permeable wall, the particles that are balanced by the imposed field and cross-flow remain within the channel and are retained in the sample. For particles where the imposed field subjects a force that is not equal to the cross-flow, the particles will move in an overall direction towards one of the permeable walls rather than remain between the walls.

At block 110, the particles remaining in the channel (i.e., those particles whose field migration velocity is opposite and equal to the cross-flow velocity) are discharged. It should be noted that the particles may migrate within a range of migration velocities that may not be exactly equal to the cross-flow but still travel through the channel and be discharged.

Since the temperature of the sample may be changed by the predetermined temperature of the cross-flow, the particles that travel through the channel are at the predetermined temperature of the cross-flow when they are discharged. Further, in one or more embodiments, a vapor-free cross-flow removes the trace vapors in the sample and thus the trace vapors are not included with the discharged particles that travel through the channel.

Subsequent actions may then process and/or use the discharged particles. In one or more embodiments, the discharged particles that travel through the channel are analyzed or scanned to determine a change in a property/characteristic of the discharged particles resulting from changing a property of the sample. In one exemplary application, a differential mobility analyzer (DMA) is used to scan the discharged particles. The discharged particles may also be collected as a classified and/or purified sample. In one or more other embodiments, the discharged particles that travel through the channel are classified based on a property of the discharged particles, for example a size, mass or charge of the discharged particles.

While particles that remain in the flow through the channel are discharged, various other particles may be removed from the flow. For example, particles that reach the permeable walls may be removed from the flow through the channel either by deposition on and adhesion to the walls or by passing through the walls.

It should be noted that the functions noted in the blocks may occur out of the order noted in FIG. 1. For example, in one or more embodiments, blocks 106 and 108 which are shown in succession may in fact occur concurrently/in parallel. In other embodiments, due to the positioning of the cross-flow, blocks 106 and 108 may occur in the reverse order, where the particles are subject to the imposed field before coming into contact with the cross-flow.

Illustrative System for Changing Sample Properties

Figure 2:
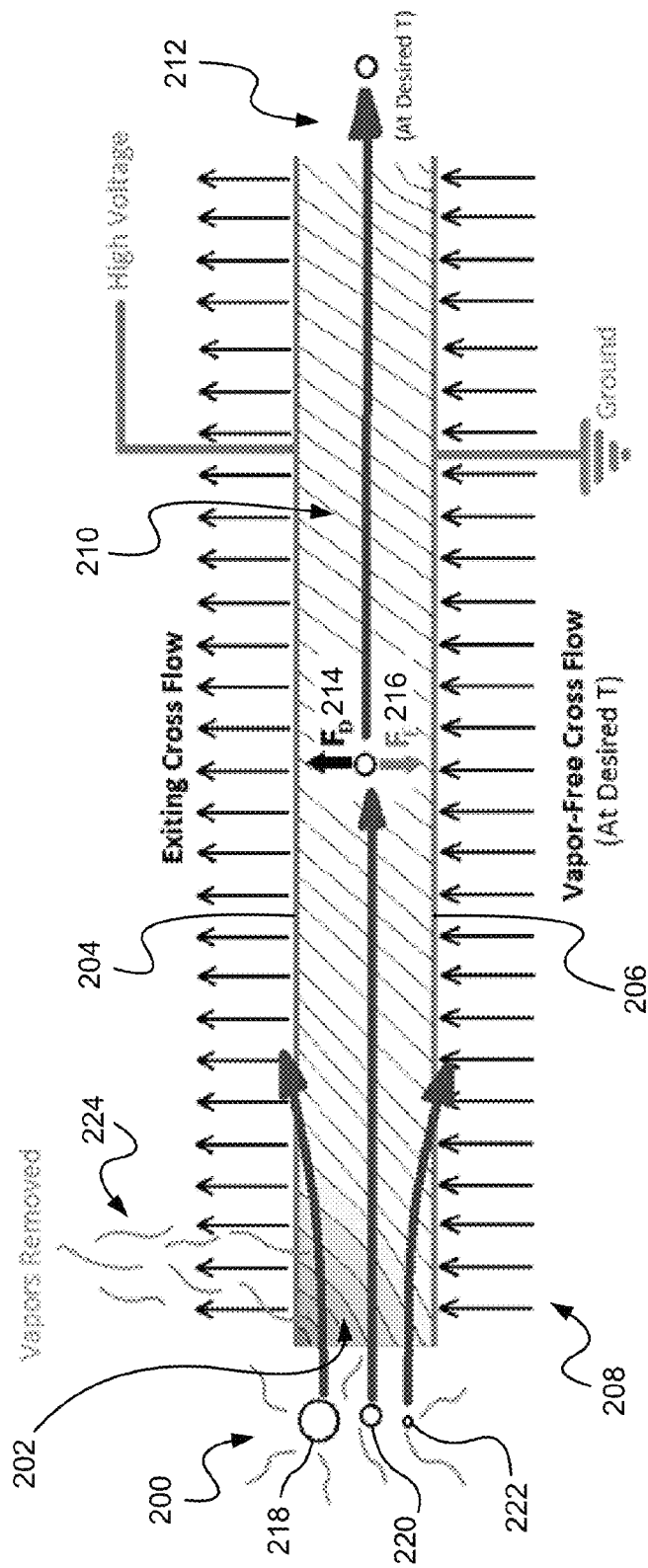
FIG. 2 illustrates the changing of various properties of a sample in accordance with one or more embodiments of the invention.

FIG. 2 is an illustrative diagram of how properties of a sample are changed in accordance with one or more embodiments of the present invention. A particulate-laden fluid sample 200 is pumped or injected into a channel 202. A pressure difference between the inlet/entrance (i.e. where the sample is injected) and outlet/exit (i.e. where the sample is discharged) regions of the channel 202 causes the sample 200 to flow in one direction through channel 202. In various embodiments, this channel 202 is part of the classification region of an OMAC. The particulate-laden sample 200 may be a polydisperse sample (i.e. comprising particles of various size, shape, and/or mass) or may be a monodisperse sample (i.e. comprising particles of uniform size, shape, and/or mass). FIG. 2 shows, for example, a polydisperse sample 200 comprising particles of various sizes, 218, 220, and 222.

The sample 200 travels between two walls 204 and 206 of channel 202 that are permeable to the flow of gases or liquids. The permeable walls 204 and 206 may include filters that can capture particles or may be made of a mesh, screen, foam, frit, honeycomb, or porous material (e.g., a porous metal such as sintered metal) that allows particles to pass through it.

A fluid cross-flow 208 enters the channel 202 through a wall 206, and exits through the opposing wall 204. The fluid cross-flow 208 follows streamlines 210 due to the orthogonal velocity of sample 200 relative to the initial velocity of cross-flow 208. The fluid cross-flow 208 may be a gas or liquid and imparts a drag force 214 ($F_D$) on the particles suspended within the sample fluid. The drag force 214 is strong enough to potentially cause all the particles in sample 200 to be lost by passing through the wall 204 or by deposition onto the wall 204.

In one or more embodiments, the cross-flow 208 is at a desired temperature predetermined by a user. As the cross-flow fluid 208 replaces the sample fluid by forcing the sample fluid out of the channel 202 through the opposing wall 204 along streamlines 210, the predetermined temperature of the cross-flow 208 rapidly replaces and changes the temperature of the sample and its particles.

In one or more further embodiments, the cross-flow 208 is vapor-less. By forcing the sample fluid out of the channel 202 through opposing wall 204 along streamlines 210, a sample fluid that includes trace vapors 224 is replaced with a cross-flow fluid 208 that is vapor-less. Thus, any trace vapors 224 that are introduced when the sample 200 is injected into the channel 202 are removed/replaced with the vapor-less cross-flow.

Additionally, an imposed field imparts a force 216 counter to the drag force 214. The imposed field can take several forms. For example, the particles 218-222 may be first charged or may already carry a charge and the imposed field may be an electric field that causes the particles 218-222 to move counter to the cross-flow 208. Likewise, the imposed field may be a magnetic field that is imposed on magnetic particles. In another example, the channel 202 is horizontal or inclined at an angle so that gravitational sedimentation counters an upward cross-flow. The channel 202 may also be arranged in a drum and spun so that centrifugal forces are imposed on the particles 218-222. Temperature differences between the two walls 204 and 206 may also be used to create a thermophoretic migration of the particles 218-222 that is counter to the cross-flow 208.

In one or more embodiments, as illustrated in FIG. 2, the imposed field is an electric field created by a conductive wall 204 at a high voltage and a conductive wall 206 at ground voltage. The voltage difference imparts an electric force ($F_E$) 216 on the particles 218-222 in a direction that is counter and opposite to the drag force 214. Depending on certain properties/characteristics of the particles 218-222, such as the size, shape, and/or mass, the electric force 216 will cause each particle 218-222 to migrate at a specific velocity towards wall 206.

Due to the advective flow of the sample 200 through channel 202, particles 218-222 of a certain property/characteristic (e.g. size, shape, mass, charge) that are substantially balanced by the drag force 214 and the force 216 created by the imposed field will traverse the classification region, while particles 218-222 that are different and subject to unbalanced forces will impact one of the walls 204 or 206. In other words, if the cross-flow 208 velocity is exactly equal but opposite to the migration velocity of the particles 218-222 due to the imposed field, the particles 218-222 will remain entrained in the sample and be carried straight though channel 202. Particles 218-222 that migrate at a higher or lower velocity than the velocity of the cross-flow 208 are transmitted to one of the walls 204 or 206. These particles 218-222 are lost through the walls 204/206 or may be disposed of, for example by deposition on and adhesion to the walls 204/206.

FIG. 2 illustrates a polydisperse sample 200, comprising particles 218, 220, and 222 of varying sizes that migrate at different velocities, which result in varying mobility separations. By adjusting the cross-flow velocity and the imposed field, a particle of a desired size 220 will remain in the channel 202 while the other particles 218 and 222 are removed. Specifically, a smaller particle 222 exits the channel 202 through wall 206 and a larger particle 218 exits through wall 204, while a particle of the desired size 220 exits through the outlet region of channel 202. In other embodiments, for example when the imposed field is gravity-based, the respective directions of larger and smaller particles 218 and 222 are opposite of that for an imposed electric field.

Note however, that for the particle 220 to reach the outlet of the channel 202, the velocity of the cross flow 208 need not be exactly equal and opposite the particle migration velocity caused by the imposed field. Particles 218-222 subject to slightly unbalanced counteracting velocities may still successfully traverse the channel 202 due to the finite length of channel 202. Particles 218-222 migrating at a velocity that is sufficiently close to and opposite the cross-flow 208 may possibly remain entrained in the sample 200 for a sufficient amount of time to travel through channel 202 and be discharged before impacting wall 204 or 206. Thus, the length of the channel 202 may be changed depending on the desired level of specificity for particles 218-222 of particular properties/characteristics (e.g., size, shape, mass, charge). Successful particle travel through a longer channel 202 would require more balanced counteracting forces on the particle 218-222, which means a smaller range of variability in the properties/characteristics (e.g., size, shape, mass, charge) of the particles 218-222 discharged. On the other hand, successful particle travel through a shorter channel 202 would require less balancing of the counteracting forces on the particle 218-222, which means a greater range of variability in the properties/characteristics (e.g., size, shape, mass, charge) of the particles 218-222 discharged.

The sample 200 comprising classified particles 218-222 of a certain property is continuously discharged from channel 202 as a classified sample flow 212. As described previously, the cross-flow 208 is able to rapidly change the temperature of the sample 200 and its particles 218-222 as well as remove any trace vapors 224 within the sample 200. Thus, as shown in FIG. 2, the discharged classified sample flow 212 is at a desired temperature, vapor-less, and comprising particles 218-222 of a desired characteristic.

Furthermore in one or more embodiments, the invention is able to change the size of the particles 218-222 within a sample 200. By changing the temperature of the sample 200, the particles 218-222 within the sample 200 are rapidly and uniformly heated or cooled as they travel through the channel 202. With the heating or cooling of the particles 218-222, the size of the particles 218-222 may be respectively increased or decreased through thermal expansion or contraction. Thus, by controlling the predetermined temperature of the cross-flow 208, the size of the discharged particles 218-222 may be controlled.

In further embodiments, the invention is able to change the chemical composition of the sample 200. In addition to removing trace vapors 224 with a vapor-free cross-flow 208, the fluid cross-flow 208 is able to remove and/or replace other compositions, vapors, and gases within a sample 200 depending on the composition of the replacement cross-flow 208. Moreover, volatile particles 218-222 or components within the sample 200 may be evaporated from the sample by heating the sample 200 with a predetermined cross-flow temperature and/or removing vapors within the sample 200, thereby decreasing in size particles 218-222. Additionally, particles 218-222 may be increased in size if the replacement cross-flow 208 is composed of vapors that can condense onto particles 218-222 and the temperature of cross-flow 208 does not prevent these additional vapors from condensing onto particles 218-222. The composition of a sample 200 may be finely controlled due to the different evaporation or condensation rates of the particles or components. If certain volatile compounds are desired in the classified sample flow 212, the cross-flow 208 will contain these compounds in the desired concentrations. These concentrations can be set at a level to condense onto and grow particles 218-222, or at a level to cause no change in the size of particles 218-222 and maintain the particle size after exiting the invention in the classified sample flow 212.

The cross-flow 208 exiting through wall 204 or the sample flow 212 exiting the channel 202 may be analyzed or scanned continuously to determine particle property/characteristic (e.g., size, mass, charge) distributions. For example, knowledge of the particle size dependence for migration velocity or mobility and the strength of the cross-flow 208 and the imposed field would enable a determination of the particle size distributions.

To allow even larger flows, multiple channels 202 may be arranged in parallel, with a single cross-flow 208 passing through the successive channels 202. In the case of electrophoretic migration, the electric potential on successive walls may be alternated, which would enable large volumetric flows to be separated without having to resort to unreasonably high voltages.

In addition, if the particles 218 and 222 are allowed to migrate through the walls 204 or 206, provision may be taken to remove the particles 218 and 222 from the cross flow 208 so that the cross-flow 208 can be re-circulated. Such provisions may include filtration of the cross-flow 208 after it exits the channel 202.

Details of Changing Sample Properties with a Radial Opposed Migration Aerosol Classifier (ROMAC)

Figure 3:
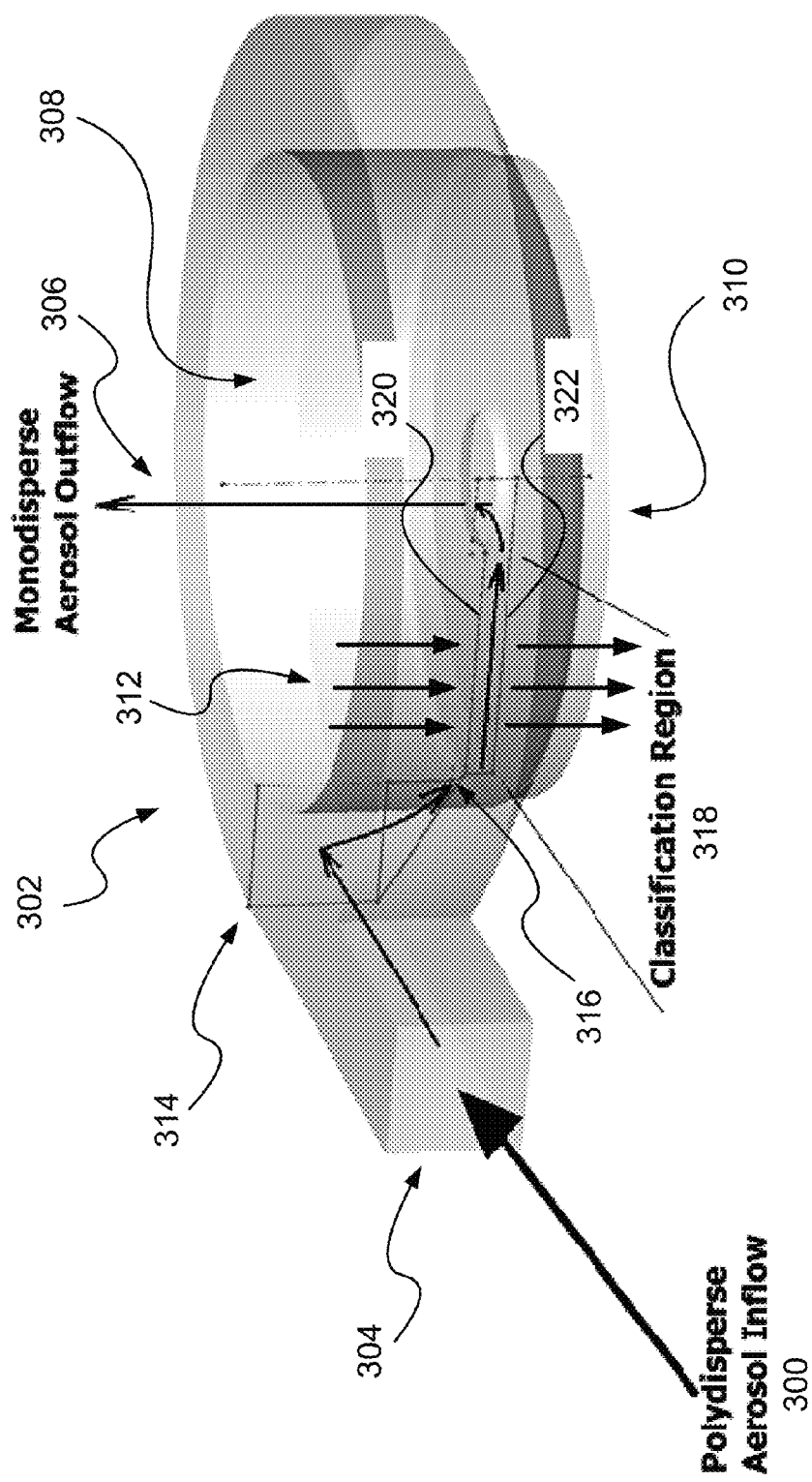
FIG. 3 illustrates a radial opposed migration aerosol classifier (ROMAC) in accordance with one or more embodiments of the invention.

In one or more embodiments of the invention, a radial opposed migration classifier (ROMAC) is used to change the properties of a sample. FIG. 3 is an illustrative diagram of how a sample 300 would traverse a ROMAC 302.

ROMAC 302 has an inlet port 304 and outlet port 306 for a sample 300, such as polydisperse, positively charged aerosol, and an inlet port 308 and outlet port 310 for a vapor-free cross-flow 312. The aerosol inlet port 304 of the ROMAC 302 would receive the sample 300, which would enter a flow distributor 314 ("racetrack"). In one or more embodiments, the sample 300 enters the flow distributor 314 tangentially. Due to the pressure difference between the racetrack 314 and the sample outlet 306, the sample 300 will be uniformly and radially drawn toward the center outlet port 306 through a narrow knife edge gap 316. After passing through the narrow knife edge gap 316, the sample 300 is now in the classification region 318, where only the particles that are balanced by both the drag and imposed field forces imparted on them will successfully traverse the classification region 318 and exit the ROMAC 302 through the central outlet port 306.

The aerosol inlet port 304 may be open to ambient fluid or connected to an apparatus that would provide the sample, such as a reaction chamber, electrospray ionization chamber, or nebulizer. The aerosol outlet port 306 may be connected to an apparatus that would provide negative pressure, such as a condensation nuclei counter pulling a vacuum. The cross-flow inlet port 308 may be connected to an apparatus that would provide vapor-free clean air at a controlled temperature and flow rate, while the cross-flow outlet port 310 may be connected to a vacuum that would result in a matched flow rate to the cross-flow inlet. In one or more embodiments, the upper plate 320 of the classification region is at electrical ground voltage, while the bottom plate 322 of the classification region is at a high positive voltage.

Figure 4:
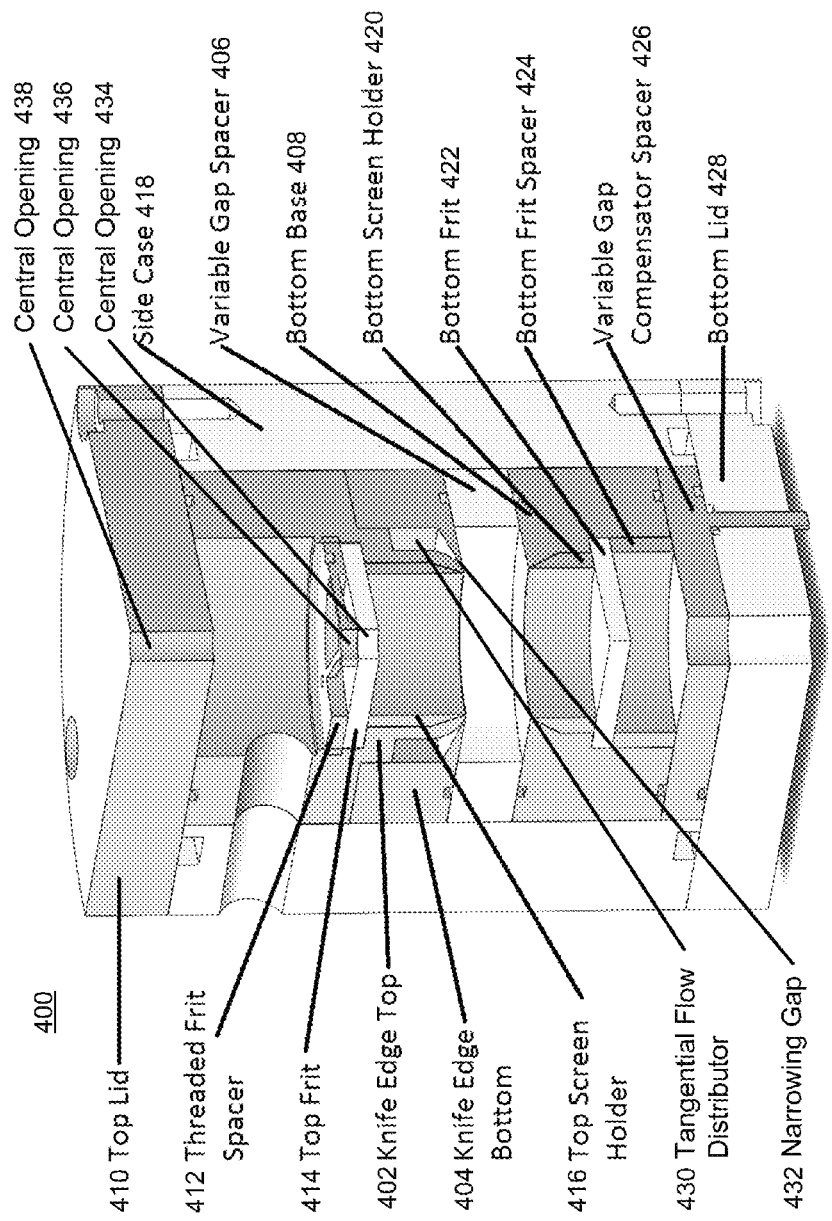
FIG. 4 illustrates a perspective view of a 2-plane sectional cut of a radial opposed migration aerosol classifier (ROMAC) in accordance with one or more embodiments of the invention.

FIG. 4 shows a perspective view of a 2-plane sectional cut of an assembled ROMAC system 400 in accordance with one or more embodiments of the invention. A top lid 410, a bottom lid 428, and a side case 418 form an outer enclosure for the system 400.

A classification region, similar to the channel 202 illustrated in FIG. 2 and channel 318 illustrated in FIG. 3, is created by a knife edge top 402, knife edge bottom 404, variable gap spacer 406, bottom base 408, and conductive, porous screens (not shown) stretched across top screen holder 416 and bottom screen holder 420. The thickness dimension of variable gap spacer 406 may be adjusted to change the space between the knife edge top 402 and bottom base 408. A top screen holder 416 and a bottom screen holder 420 are used to hold respective top and bottom permeable walls, such as stretched stainless steel mesh (not shown). A top frit 414 and bottom frit 422 serve to laminarize the cross-flow before it enters the classification region. The top frit 414 is held in place and may be positionally adjusted within the system 400 by a threaded frit spacer 412. Similarly, bottom frit 422 is held in place and may be positionally adjusted within the system 400 by a bottom frit spacer 424.

Additionally, the top frit 414, threaded frit spacer 412, and top lid 410 all include central openings 434, 436, and 438 for a single outlet tube (not shown) to pass through the respective central openings 434, 436, and 438 and rest on a screen stretched across top screen holder 416. The single outlet tube is connected to the classification region and provides a negative pressure that allows particles that are balanced by both the drag and imposed field forces to be discharged from the system 400 through the single outlet tube (not shown).

A flow distributor 430 includes a narrowing gap 432, similar to the narrow knife gap 316 illustrated in FIG. 3, which leads to the classification region. The narrowing gap 432 is created by the knife edge top 402 and knife edge bottom 404. In one or more embodiments, the sample is introduced tangentially into the flow distributor 430.

In one or more embodiments, top lid 410, knife edge top 402, knife edge bottom 404, top screen holder 416, top frit 414, threaded frit spacer 412, and the outlet tube (not shown) that passes through central openings 434-438 and rests on a conductive screen (not shown) stretched across top screen holder 416 are at electrical ground. Side case 418, variable gap spacer 406, and bottom lid 428 are electrical insulators. Bottom base 408, bottom screen holder 420, bottom frit 422, bottom frit spacer 424, variable gap compensator spacer 426, and a conductive screen (not shown) stretched across bottom screen holder 420 are at a non-ground electrical potential. A post 446 extends from variable gap compensator spacer 426 through bottom lid 428 serves as a means to apply a non-ground electric potential.

Illustrative Models and Simulations

Figure 5:
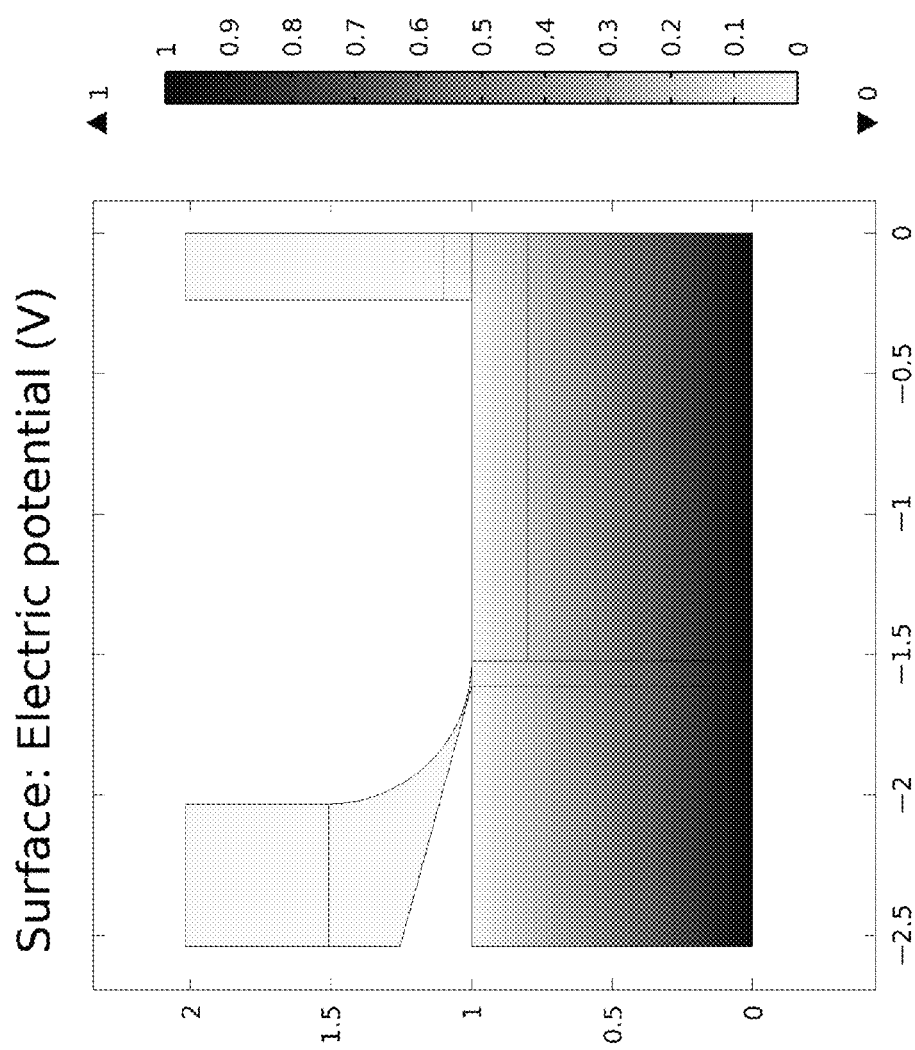
FIG. 5 illustrates an electric potential distribution model of a solution flowing through a section of a radial opposed migration aerosol classifier (ROMAC) in accordance with one or more embodiments of the invention.
Figure 6:
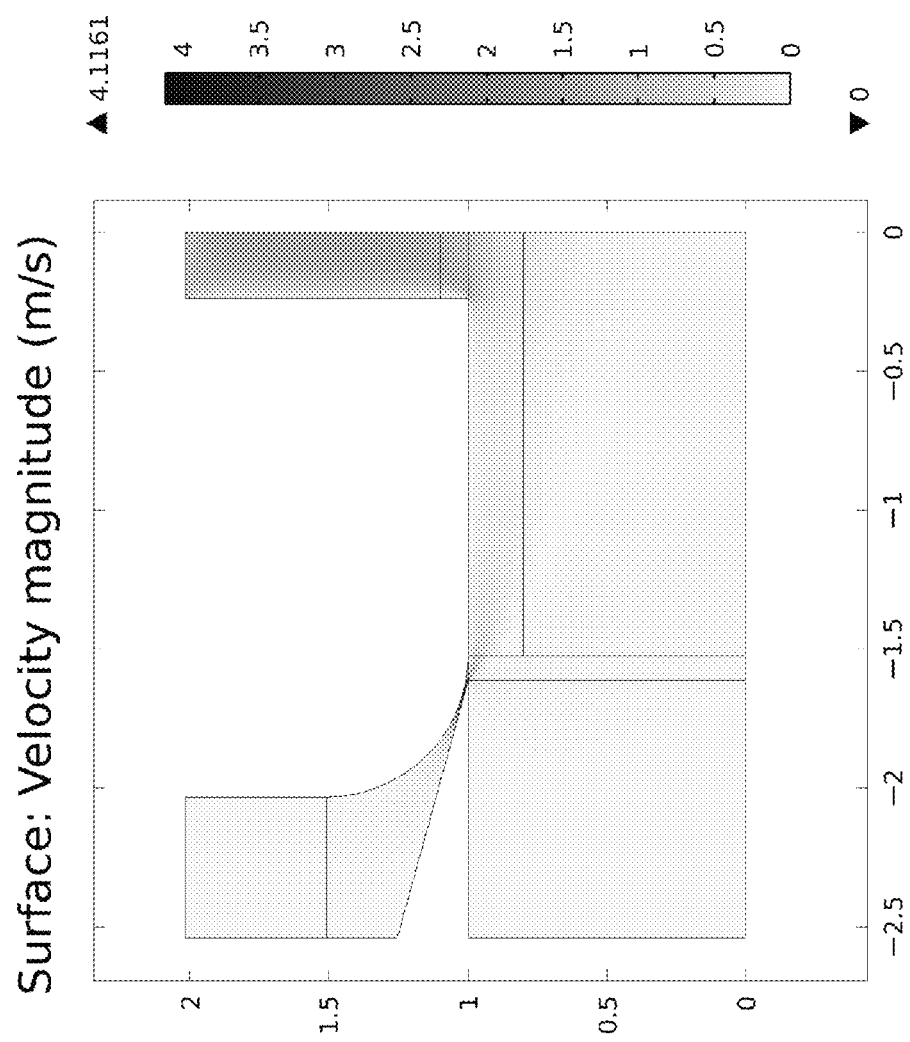
FIG. 6 illustrates a fluid velocity distribution model of a solution flowing through a section of a radial opposed migration aerosol classifier (ROMAC) in accordance with one or more embodiments of the invention.
Figure 7:
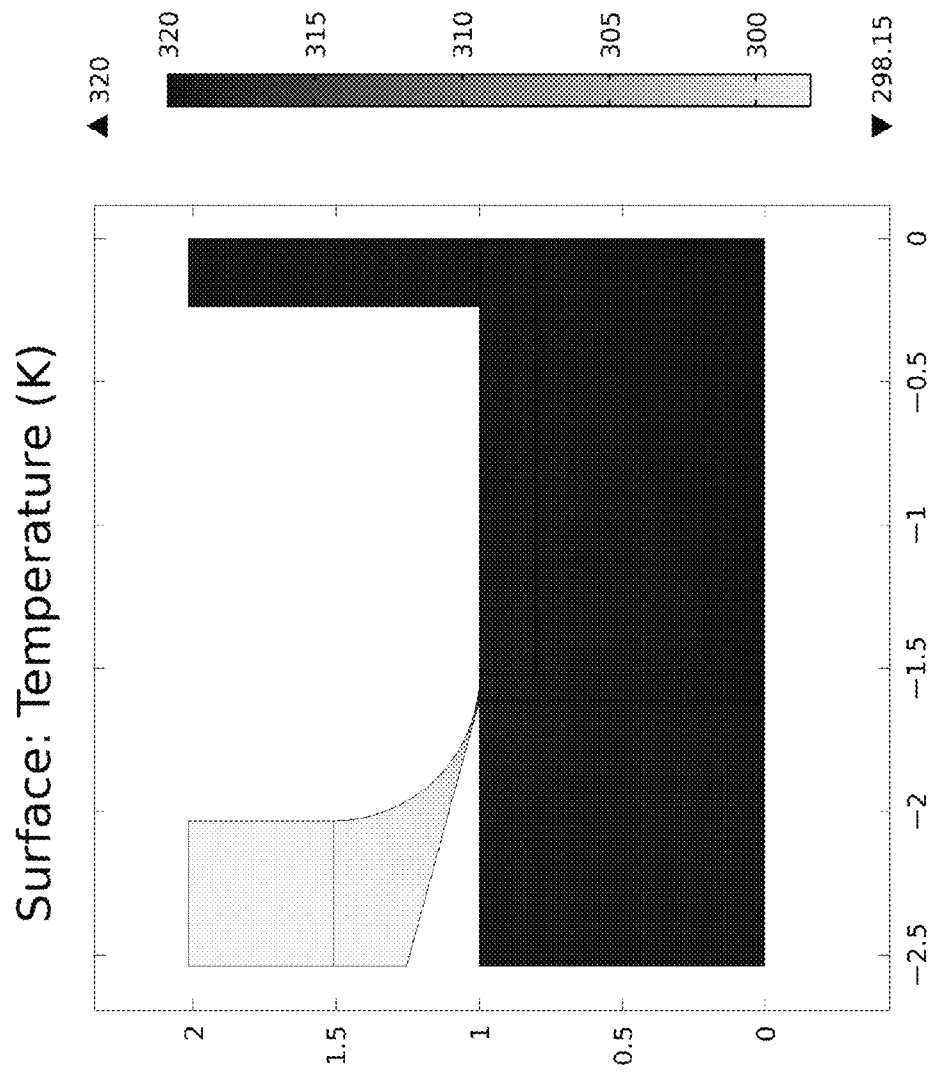
FIG. 7 illustrates a fluid temperature distribution model of a solution flowing through a section of a radial opposed migration aerosol classifier (ROMAC) in accordance with one or more embodiments of the invention.
Figure 8:
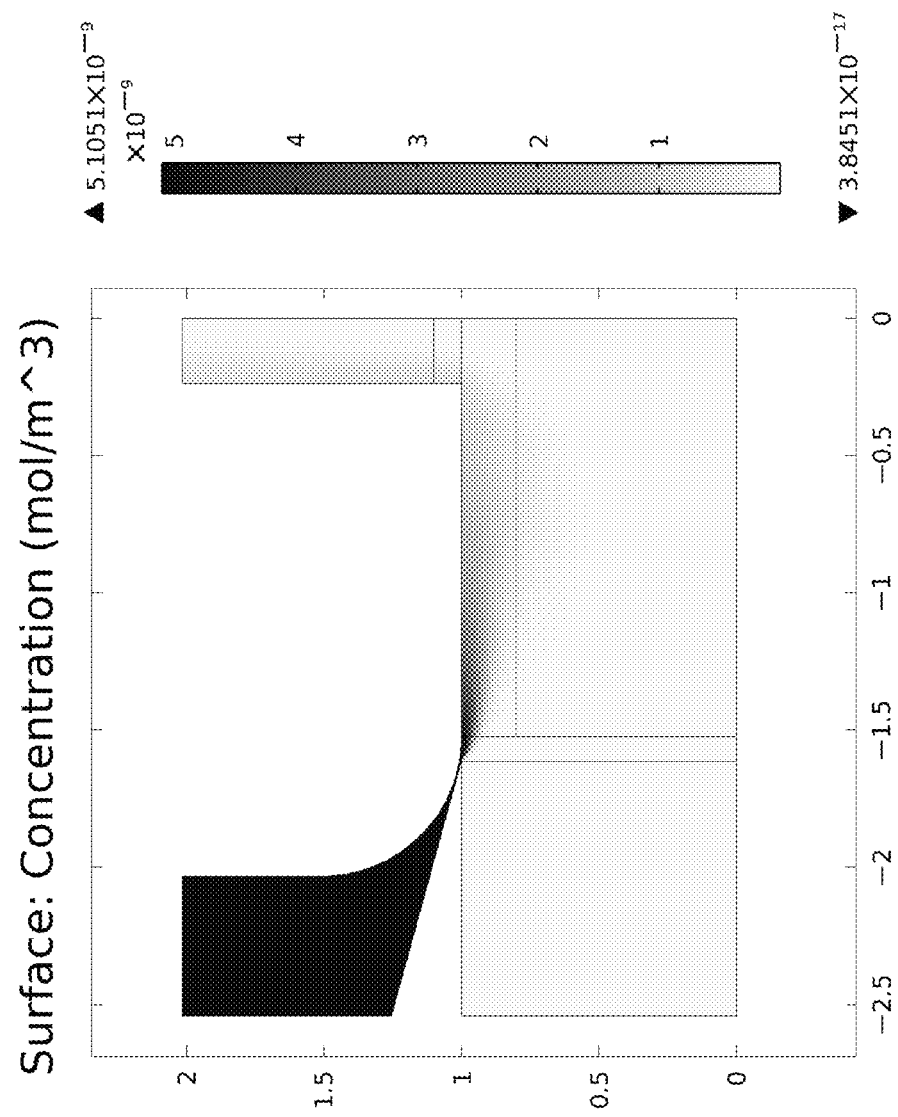
FIG. 8 illustrates a trace vapor concentration distribution model of a solution flowing through a section of a radial opposed migration aerosol classifier (ROMAC) in accordance with one or more embodiments of the invention.

As illustrative examples, the invention was modeled as a radially symmetric space similar to the ROMAC 302 depicted in FIG. 3 in COMSOL™ Multiphysics 4.1™ to obtain values for fluid properties, fluid flows, electric fields, and concentrations of dilute vapors in the region of the invention through which aerosol particles will flow through. The electric potential solution is shown in FIG. 5, the combined sample and cross-flow fluid velocity magnitude solution is shown in FIG. 6, the fluid temperature solution is shown in FIG. 7, and the dilute species vapor concentration is shown in FIG. 8. All four of the figures were modeled at an aerosol flow rate of 1 lpm and a cross-flow rate of 2 lpm, with a cross-flow temperature of 320 K, an incoming aerosol vapor concentration of 5.1 mol/m$^3$, and an incoming sample vapor diffusivity of 5.8×10$^{-6}$ m$^2$/s.

FIG. 7 demonstrates that the invention as modeled sufficiently exchanges the gas such that it is rapidly and uniformly heated to the desired temperature (in this case, 320 K) by the time the particles reach the aerosol outlet.

FIG. 8 demonstrates that the invention as modeled sufficiently removes the trace vapors present in the original incoming aerosol gas, such that by the time the particles reach the aerosol outlet, they are surrounded in vapor-free fluid.

The COMSOL™ solutions were then used as inputs for a MATLAB™ script developed to simulate the trajectories of particles of a particular size when released into the invention. The trajectories used inputs of fluid velocity, density, viscosity, temperature, and electric potential to simulate the movement of particles, their change in size, and the change in chemical composition in finite time steps. In addition, diffusional movement of the particles was simulated as well.

Figure 9:
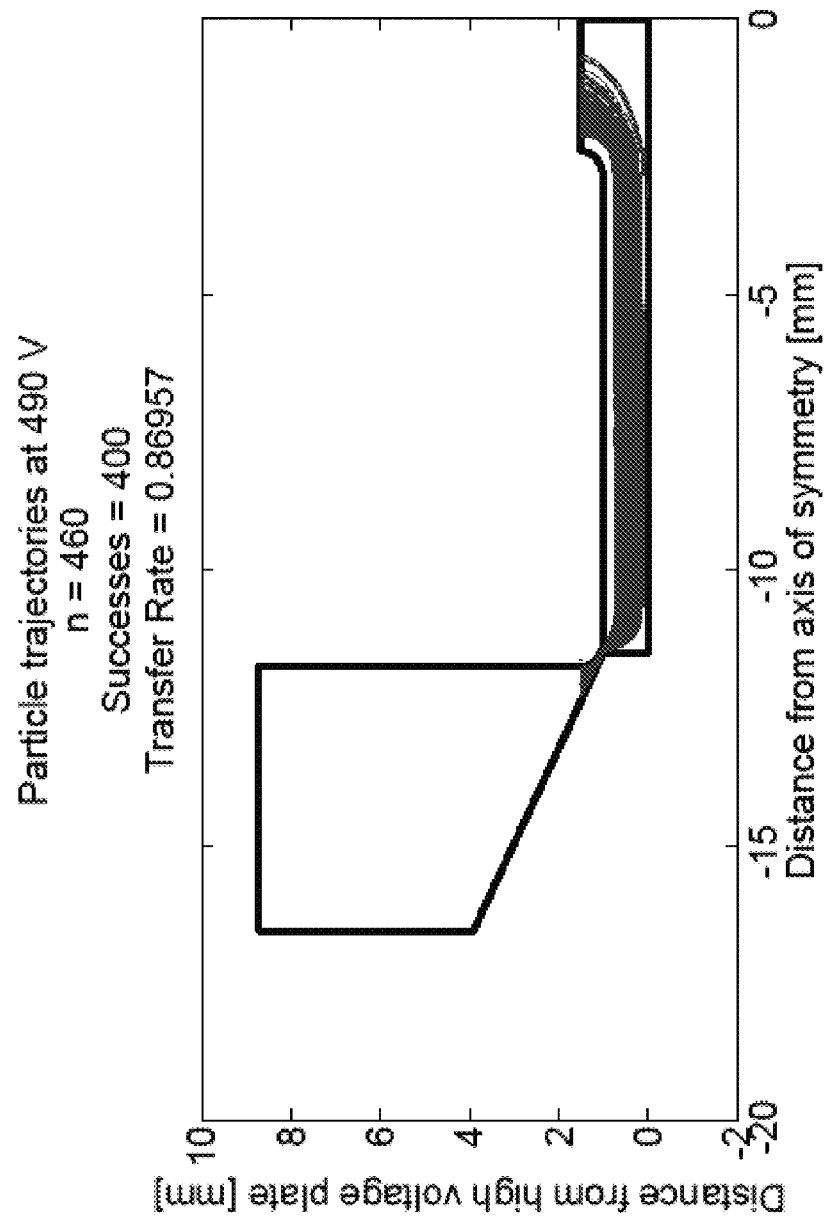
FIG. 9 illustrates a particle trajectories simulation model of a solution flowing through a section of a radial opposed migration aerosol classifier (ROMAC) in accordance with one or more embodiments of the invention.

FIG. 9 shows a simulation of 100 nm particles composed of three organic substances with different volatilities traversing the invention with the porous, conductive walls having a voltage difference that was predicted to yield the maximum transmission of particles through the classification region. The aerosol flowrate was set at 0.1 lpm, cross-flow rate at 0.3 lpm, temperature at 320 K, and voltage at 490 V. The type of simulation illustrated in FIG. 9 was repeated at various voltages to obtain a predicted transfer function (FIG. 10) for the invention. The results demonstrate the feasibility of the invention, as the numerical simulations were executed with well-reputed software and relied on the established knowledge of mechanisms of particle movement.

Figure 10:
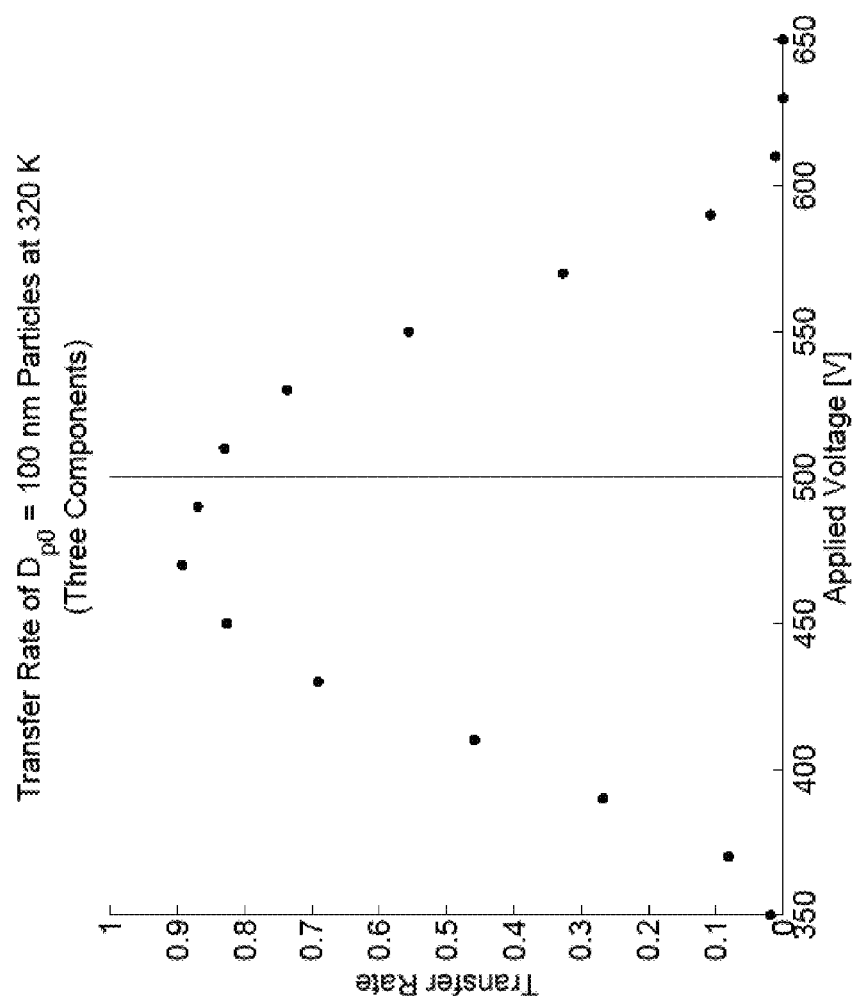
FIG. 10 illustrates a particle transfer simulation model of a solution flowing through a section of a radial opposed migration aerosol classifier (ROMAC) in accordance with one or more embodiments of the invention.

FIG. 10 illustrates a simulated transfer function of 100 nm particles traversing through the invention at an aerosol flow rate of 0.1 lpm, cross-flow rate of 0.3 lpm, and temperature at 320 K. The vertical line indicates the theoretical voltage that would result in a balance of the drag force and electric force imparted on the particles (which would result in maximum transmission, i.e. 100% transmission of the particles). The peak of the simulated transfer function is in very good agreement with the theoretical voltage for 100% transmission, but is slightly shifted to the left, since particles were slowly evaporating and shrinking as they were traversing the classification region, due to the heat and gas exchanging functions of the instrument.

Figure 11:
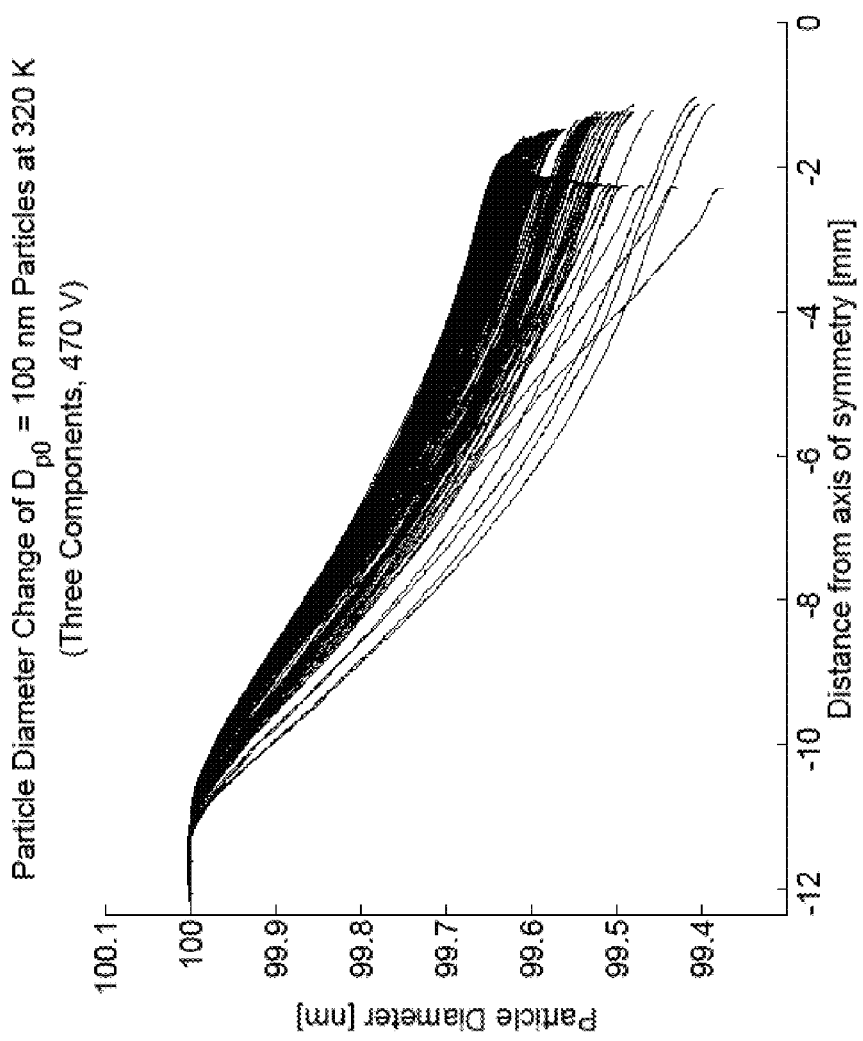
FIG. 11 illustrates a particle diameter change simulation model of a solution flowing through a section of a radial opposed migration aerosol classifier (ROMAC) in accordance with one or more embodiments of the invention.

FIG. 11 illustrates the simulated diameter change of each individual 100 nm particle, showing each particle's size evolution as it traverses the invention. The aerosol flow rate is set at 0.1 lpm, cross-flow rate at 0.3 lpm, temperature at 320 K, and voltage at 470 V.

Figure 12:
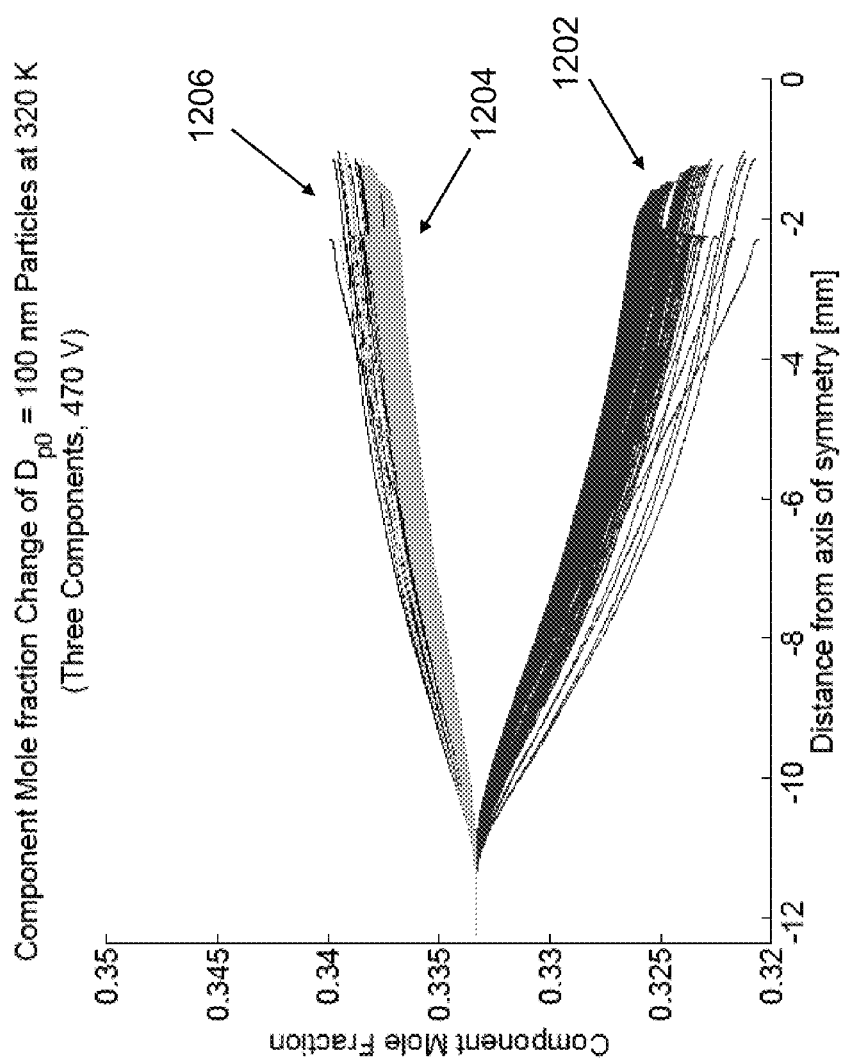
FIG. 12 illustrates a particle chemical composition change simulation model of a solution flowing through a section of a radial opposed migration aerosol classifier (ROMAC) in accordance with one or more embodiments of the invention.

FIG. 12 illustrates the simulated chemical composition change of 100 nm particles traversing through the invention an aerosol flow rate of 0.1 lpm, cross-flow rate of 0.3 lpm, temperature of 320 K, and voltage of 470 V. Initial chemical composition is 33% of each of 3 species 1202, 1204, and 1206. 1202 is the most volatile species, followed by 1204, followed by 1206 being the least volatile species. The chemical composition change of each particle is shown as different components of the particles evaporate at different rates due the heat and vapor removal functions of the invention.

CONCLUSION

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. All publications, patents, and patent applications cited herein are hereby incorporated by reference in their entirety for all purposes.

REFERENCES

[1] Liu, B., et al., Aerosol Mobility Chromatograph-New Detector for Sulfuric-Acid Aerosols. *Atmos Environ,* 1978, 12(1-3): p. 99-104.

[2] Rader, D. and P. McMurry, Application of the Tandem Differential Mobility Analyzer to Studies of Droplet Growth or Evaporation. *J Aerosol Sci,* 1986, 17(5): p. 771-787.

[3] Flagan, R., Cross-flow differential migration classifier. U.S. Pat. No. 6,905,029.

[4] Flagan, R., Opposed migration aerosol classifier (OMAC), *Aerosol Science and Technology,* 2004, 38(9): p. 890.

[5] Downard, A., J. Dama, and R. Flagan, An Asymptotic Analysis of Differential Electrical Mobility Classifiers, *Aerosol Science and Technology,* 2011, p. 717-729.

[6] Knutson, E. and K. Whitby, Aerosol classification by electric mobility: apparatus, theory, and applications, *J Aerosol Sci,* 1975, p. 443-451.

[7] Tammet, H., Symmetric Inclined Grid Mobility Analyzer for the Measurement of Charged Clusters and Fine Nanoparticles in Atmospheric Air, *Aerosol Science and Technology,* 2011, p. 468-479.

What is claimed is:

1. A method for changing a property of a sample comprising:

introducing a sample, comprising one or more particles suspended within a sample fluid, through a channel, wherein the channel comprises two walls that are permeable to a flow of fluid;

introducing a fluid cross-flow of a predetermined chemical composition and at a predetermined temperature to the channel through one of the permeable walls, wherein the fluid cross-flow flows at a first velocity and exits in a first direction through the other permeable wall;

applying an imposed field on the one or more particles in a second direction counter to the first direction of the fluid cross-flow, wherein the imposed field causes the one or more particles to migrate at a second velocity opposite and/or equal to the first velocity of the fluid cross-flow; and continuously discharging the particles that travel through the channel, wherein the particles that travel through the channel are discharged in a fluid of the predetermined chemical composition and at the predetermined temperature of the fluid cross-flow, and wherein a size and/or chemical composition of the one or more particles of the sample is changed by the predetermined chemical composition and/or predetermined temperature of the fluid cross-flow while the one or more particles travel through the channel.

2. The method of claim 1, wherein the sample fluid is substantially replaced by the fluid cross-flow as the sample flows through the channel, whereby the discharged particles that travel through the channel are suspended within the fluid cross-flow.

3. The method of claim 1, wherein the fluid cross-flow removes a trace vapor from the sample.

4. The method of claim 1, wherein a chemical composition of the sample is changed while the one or more particles of the sample travel through the channel.

5. The method of claim 1, further comprising charging the one or more particles in the sample, wherein the imposed field is an electric field.

6. The method of claim 1, further comprising analyzing or scanning the discharged particles that travel through the channel to determine a change in a property of the discharged particles resulting from changing a property of the fluid through which the particles travel.

7. The method of claim 6, wherein a differential mobility analyzer is used to scan the discharged particles.

8. The method of claim 1, further comprising classifying the discharged particles that travel through the channel based on a property of the discharged particles.

9. The method of claim 8, wherein the property of the discharged particles is a size, mass or charge of the discharged particles.

10. An opposed migration classifier comprising:

a channel through which passes a sample comprising one or more particles suspended within a sample fluid, wherein the channel comprises two walls that are permeable to a flow of fluid;

a fluid cross-flow of a predetermined chemical composition and at a predetermined temperature that enters the channel through one of the permeable walls, wherein the fluid cross-flow flows at a first velocity and exits in a first direction through the other permeable wall;

an imposed field that is applied on the one or more particles in a second direction counter to the first direction of the fluid cross-flow, wherein the imposed field causes the one or more of the particles to migrate at a second velocity opposite and/or equal to a first velocity of the fluid cross-flow; and wherein the particles that travel through the channel are discharged in a fluid of the predetermined chemical composition and at the predetermined temperature of the fluid cross-flow, and wherein a size and/or chemical composition of the one or more particles of the sample is changed by the predetermined chemical composition and/or predetermined temperature of the fluid cross-flow while the one or more particles travel through the channel.

11. The opposed migration classifier of claim 10, wherein the sample fluid is substantially replaced by the fluid cross-flow as the sample flows through the channel, whereby the discharged particles that travel through the channel are suspended within the fluid cross-flow.

12. The opposed migration classifier of claim 10, wherein the fluid cross-flow removes a trace vapor from the sample.

13. The opposed migration classifier of claim 10, wherein a chemical composition of the sample is changed while the one or more particles of the sample travel through the channel.

14. The opposed migration classifier of claim 10, wherein:
the one or more particles in the sample is charged; and
the imposed field is an electric field.

15. The opposed migration classifier of claim 10, wherein the discharged particles that travel through the channel are analyzed or scanned to determine a change in a property of the discharged particles resulting from a change in a property of the fluid through which the particles travel.

16. The opposed migration classifier of claim 15, wherein a differential mobility analyzer is used to scan the discharged particles.

17. The opposed migration classifier of claim 10, wherein the discharged particles that travel through the channel are classified based on a property of the discharged particles.

18. The opposed migration classifier of claim 17, wherein the property of the discharged particles is a size, mass or charge of the discharged particles.

19. A method for changing a property of one or more particles in a sample comprising:
introducing a sample, comprising one or more particles suspended within a sample fluid, through a channel, wherein the channel comprises two walls that are permeable to a flow of fluid;
introducing a fluid cross-flow of a predetermined chemical composition and/or at a predetermined temperature to the channel through one of the permeable walls, wherein the fluid cross-flow flows at a first velocity and exits in a first direction through the other permeable wall;
applying an imposed field on the one or more particles in a second direction counter to the first direction of the fluid cross-flow, wherein the imposed field causes the one or more particles to migrate at a second velocity opposite and/or equal to the first velocity of the fluid cross-flow; and
continuously discharging the particles that travel through the channel, wherein the particles that travel through the channel are discharged in a fluid of the predetermined chemical composition and at the predetermined temperature of the fluid cross-flow, and wherein a property of the one or more particles of the sample is changed by the predetermined chemical composition and/or predetermined temperature of the fluid cross-flow while the one or more particles travel through the channel.

20. The method of claim 19, wherein the property of the one or more particles is a size, mass or chemical composition of the discharged particles.

* * * * *